United States Patent
Mohr

(10) Patent No.: US 7,639,852 B2
(45) Date of Patent: Dec. 29, 2009

(54) METHOD FOR ASSOCIATING DATA WITH MEDICAL IMAGE DATASETS

(75) Inventor: Cecile Mohr, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 688 days.

(21) Appl. No.: 11/378,144

(22) Filed: Mar. 16, 2006

(65) Prior Publication Data
US 2006/0251305 A1 Nov. 9, 2006

(30) Foreign Application Priority Data
Mar. 16, 2005 (DE) .................. 10 2005 012 154

(51) Int. Cl.
G01K 9/00 (2006.01)
A61B 5/00 (2006.01)
(52) U.S. Cl. ...................... 382/128; 600/300
(58) Field of Classification Search .......... 382/128, 382/129, 130, 131, 132, 133, 134; 600/300, 600/407, 410, 431, 437, 411, 427, 443, 444, 600/445, 447; 705/2, 3; 707/3, 130 Z, 201; 128/920, 906, 916
See application file for complete search history.

(56) References Cited

U.S. PATENT DOCUMENTS

| 6,511,426 | B1 * | 1/2003 | Hossack et al. ............ 600/437 |
| 6,678,703 | B2 * | 1/2004 | Rothschild et al. .......... 707/201 |
| 2002/0016718 | A1 | 2/2002 | Rothschild et al. |
| 2004/0147840 | A1 | 7/2004 | Duggirala et al. |
| 2005/0004938 | A1 | 1/2005 | Koenig |
| 2005/0021512 | A1 | 1/2005 | Koenig |

FOREIGN PATENT DOCUMENTS

WO   WO 2005/017806   2/2005

OTHER PUBLICATIONS

"A Structured Report Dataset for Documentation of Echocardiographic Studies—Update 2004," Voelker, Z. Kardiol., vol. 93 (2004) pp. 987-1004.
"Feature Based Retrieval of Echocardiographic Images Using DICOM Structured Reporting," Nedevschi et al., Computers in Cardiology, vol. 28, (2001), pp. 679-682.
"HL7 Clinical Document Architecture to Share Cardiological Images and Structured Data in Next Generation Infrastructure," Marcheschi et al., Computers in Cardiology, vol. 31, (2004), pp. 617-620.

* cited by examiner

Primary Examiner—Abolfazl Tabatabai
(74) Attorney, Agent, or Firm—Schiff Hardin LLP

(57) ABSTRACT

In a method for association of data with medical image datasets, at least one region is established on an overview image of an examination subject and data are associated with the region. At least one image dataset is associated with the region, and the data are thereupon automatically associated with the at least one image dataset using the at least one region.

7 Claims, 3 Drawing Sheets

METHOD FOR ASSOCIATING DATA WITH MEDICAL IMAGE DATASETS

BACKGROUND OF THE INVENTION

1. Field of the Invention

The present invention concerns a method for association of data with medical image datasets.

2. Description of the Prior Art

In imaging diagnostics, for example by means of magnetic resonance examinations, image datasets of a patient are acquired. These can be, for example, whole-body exposures or local exposures of a particular region or organ of the patient. To generate a diagnosis or a finding, it is frequently necessary to send the finding to appropriate specialists. Given extensive examinations with many image datasets, this in particular requires a high logistical effort since each image dataset must be evaluated individually. Given whole-body exposures it would also be possible to present the entire exposure to each of the specialists for medical assessment, but this would entail a high time commitment for the specialized doctor or radiologist. This is in particular problematic in the event that the specialized doctor or radiologist is not qualified for medical assessment of each body region under the circumstances.

SUMMARY OF THE INVENTION

An object of the present invention is to provide a method that allows image datasets to be provided with supplementary information in a simple manner.

This object is achieved in accordance with the invention by a method wherein at least one region on an overview image of an examination subject (for example a patient) is established. Data are thereafter associated with this (at least one) region. An automatic association of at least one image dataset with the at least one region and an automatic association of the data with the at least one image dataset using the at least one region follow. In the inventive method, supplementary information that are associated using a selected region (for example that of the patient) can be associated in a simple manner with the image datasets that generally exist in larger number after an examination. In this manner, every image dataset does not have to be individually provided with the supplementary information. The data only have to be associated once with each region on the overview image, whereupon all image datasets associated with the region are provided with the corresponding data.

The data are predetermined and can be selected in an embodiment of the method. This makes the association of the data with the regions easier.

In the inventive method, the data are automatically evaluated. For example, using the stored information about each specialist for medical assessment it is thereby possible to send the corresponding image datasets to the appropriate specialists for medical assessment in an automated manner, for example via electronic mail.

In an embodiment, the image dataset is divided into a number of partial image datasets using the established regions and data are associated with the number of partial image datasets. This is in particular reasonable in the case of whole-body exposures that are then divided into a number of sub-regions and provided with the corresponding data. Given existing whole-body exposures, the corresponding regions can also be made accessible to the respective specialists for generation of a diagnosis.

DESCRIPTION OF THE PREFERRED EMBODIMENTS

The method described in the following concerns the processing of image datasets that were acquired by means of magnetic resonance examinations. The method is, however, also is applicable to other imaging examination methods such as, for example, computed tomography or positron emission tomography.

Figure 1:
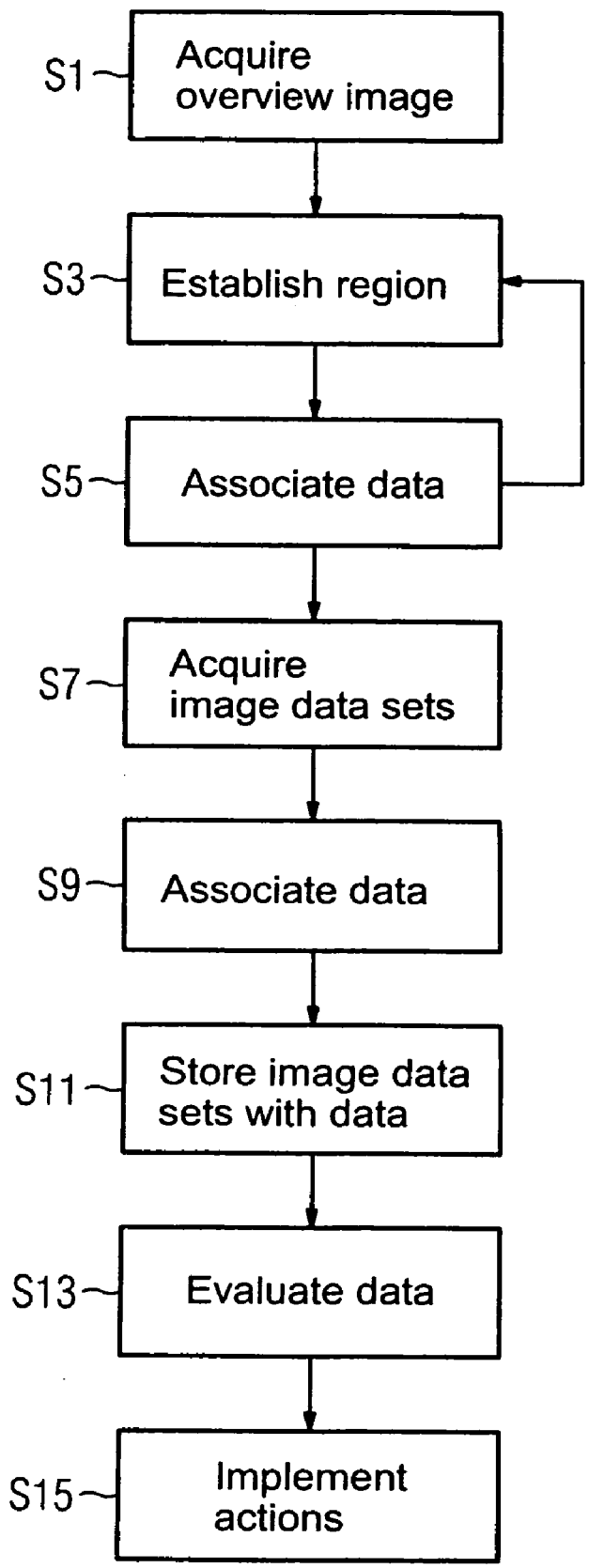
FIG. 1 is a flowchart of a preferred embodiment of the invention.

As shown in FIG. 1, an overview image is acquired in a first method step S1. This can be a magnetic resonance image with lower quality, since here only the regions are established. In a second method step S3, the overview image is displayed on a display medium (for example a monitor), whereupon a user can establish a region. The region is established via dragging with a computer mouse. This also can be seen in FIGS. 2 through 3. In a third method step S5, corresponding data are associated with the region. This occurs, for example, via a pull-down menu in which a number of data items that can be respectively associated with the region are available for selection. The data can represent various information about the region. A designation and a comment are thus present for the region. Furthermore, instructions for further processing are contained in the data. For example, a preferred storage location (for example on a server connected over a network) or name and e-mail address of a corresponding specialized doctor can be stored. The data can be changed by the user. Moreover, it is possible for the user to input new data. This is, for example, necessary when a previously not-yet-established region should be used for the first time and the previously defined data do not match the region, or when new data should be added to a region. The second method step S3 and third method step S5 can be implemented multiple times in succession in order to establish multiple regions on the overview image and to associated data with them. The entire body of a patient thus can be divided into regions.

Image datasets are acquired in a fourth method step S7. At least one region is associated with each image dataset. If one of the image datasets contains areas that belong to multiple regions, it is associated with the corresponding regions. In both cases the association ensues automatically. Alternatively, it is possible to divide the image dataset into partial image datasets using the defined region. This is meaningful, for example, in the case of image datasets that image the head and upper body of the patient. The corresponding image dataset contains parts of the abutting regions "head" and "upper body" and is correspondingly divided into two partial image datasets. After the division, one of the partial image datasets contains the image data from the region "head", the other contains the image data of the region "upper body". Moreover, it is possible to subsequently associate already-measured image datasets with the regions, which also advantageously ensues in an automated manner. In each case it is possible for the user to display and to change the association of the region with the image datasets. The division into partial image datasets can also ensue manually.

In a fifth method step S9, the data that are associated with the corresponding region are automatically associated with the image datasets. This no longer has to occur manually via the user for each of the image datasets. In a sixth method step S11, the image datasets are stored together with the corresponding data. The associated data are stored in the DICOM header of the respective image dataset. An automatic evaluation of the data ensues in a seventh method step S13. Using the data it is determined what should happen with the image datasets, thus, for example, where they should be stored or to which radiologists they should be sent. Appropriate actions to that end are implemented in an eighth method step S15. Given corresponding data such an action can be, for example, sending the corresponding image datasets to an associated specialized doctor for medical assessment.

Figure 2:
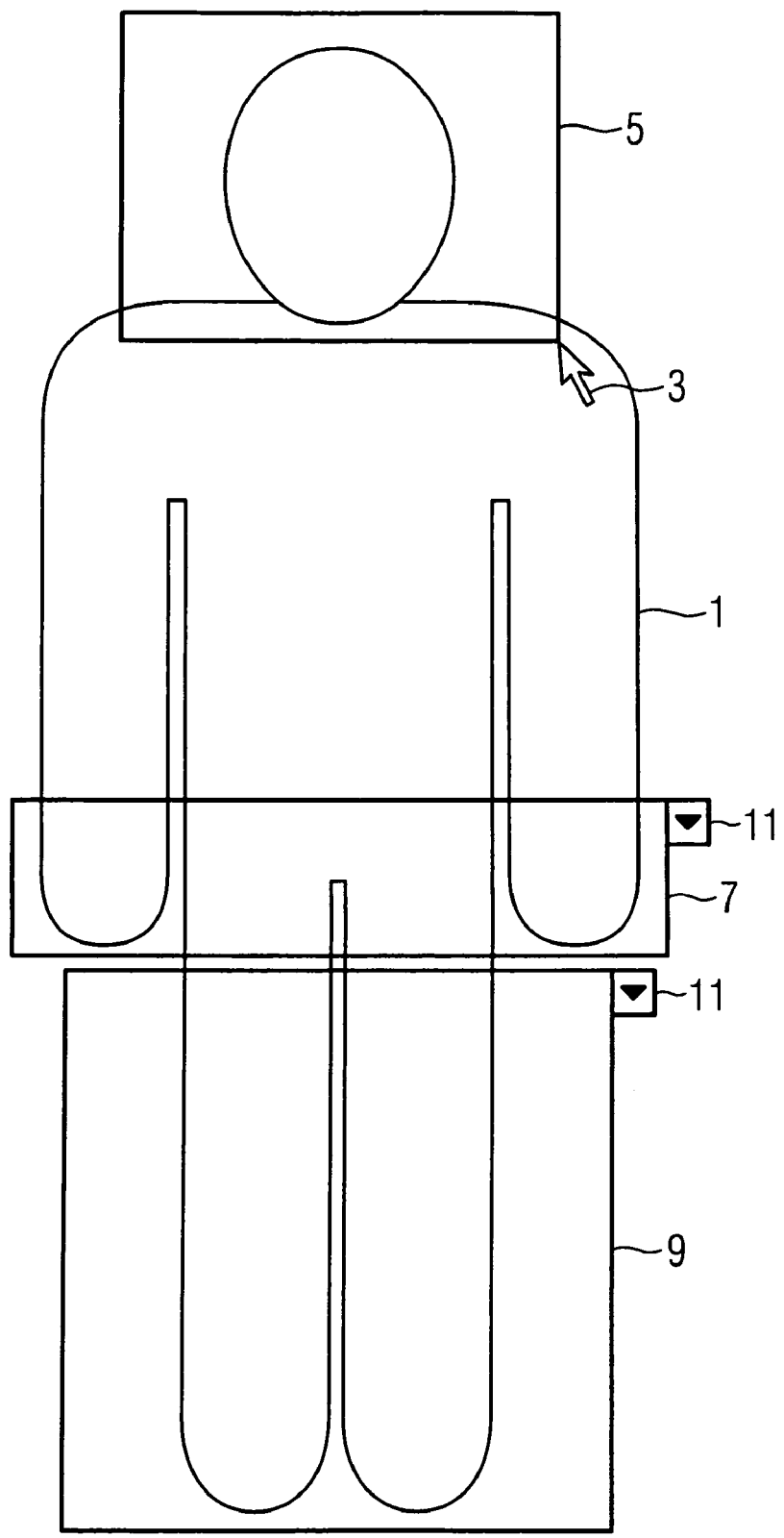
FIG. 2 schematically shows an overview image with a selected region.

A schematic overview image of a whole-body exposure 1 of a patient is shown in FIG. 2. This can be either an image with low resolution serving as the overview, or a whole-body examination with high resolution that is later further processed for medical assessment. Rectangular regions 5, 7 and 9 that define respective regions of the body of the patient can be drawn by means of a computer mouse, which here is symbolized by a mouse pointer 3. The regions 7 and 9, one over the legs and one in the back area, are already defined in FIG. 2, while the region 5 is directly drawn around the head area by means of the mouse pointer 3. The size of the regions 5, 7 and 9 can subsequently be enlarged or reduced or displaced by simple dragging with the mouse pointer 3 on the border of the respective region. The association of data with the respective regions 5, 7 and 9 occurs via a pull-down menu that is displayed on the respective region by a mouse click on the menu button 11. This is explained in connection with FIG. 3.

Figure 3:
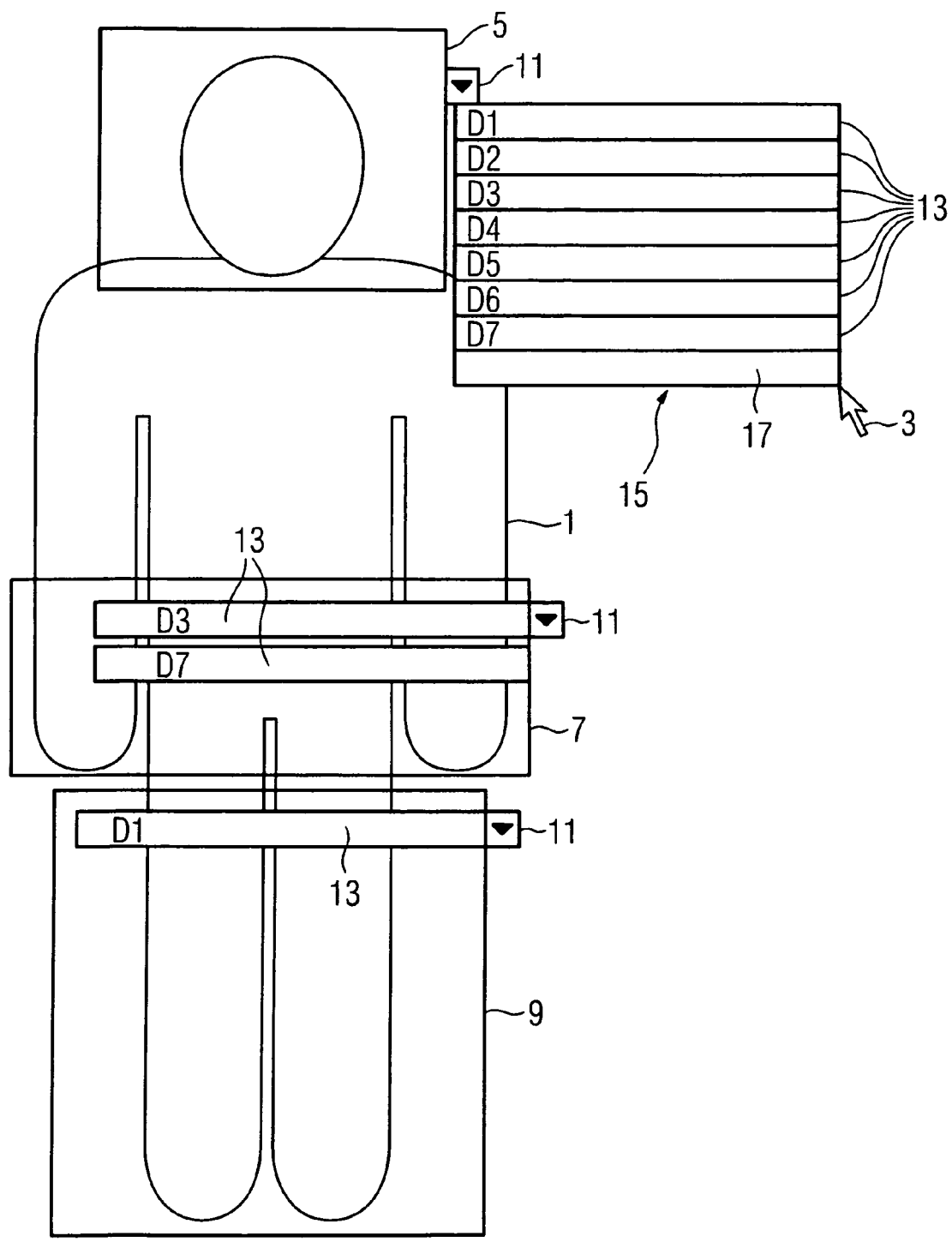
FIG. 3 is a further schematic illustration of an overview image with selected regions.

FIG. 3 shows the overview image from FIG. 2, wherein data 13 are already associated with the regions 7 and 9 around the legs and the back area. The corresponding data 13 are displayed in the region, such that a direct and simple monitoring by the user is possible. Further data can be associated with each region 7 or 9 using the corresponding menu button 11. By dragging already-associated data from the region 7 or 9 with the mouse, already-associated data can be removed again from the region 7 or 9.

The pull-down menu 15 at the region 5 has been opened with a mouse click on the corresponding menu button 11. In this state, various entries for data 13 can be selected with the mouse pointer 3. The data are symbolically designated with D1 through D7. It is likewise possible to add new data by clicking on an empty data line 17. The new data are automatically stored in a databank with corresponding data and displayed in the pull-down menu upon following recall. Multiple types are available for selection as data 13, so a number of data items can be associated with any region 5, 7, or 9. A designation (such as "head", "back" or "legs" in the present example) is to be associated with each region 5, 7 or 9. Data 13 are likewise present that contain various actions that are associated with the corresponding regions 5, 7 or 9 and are executed for further processing of the corresponding image datasets. Among other things, these actions include the archiving or sending to a specialized doctor. In the present example, a corresponding entry "D7" is already selected for the region 7.

In the case of a high-resolution whole-body exposure 1, it is likewise possible to divide the image dataset into a number of partial image datasets by means of the correspondingly-defined regions 5, 7 and 9 and to provide the image dataset with the corresponding data 13. Parts of a whole-body exposure 1 can thus also be associated with appropriate specialists for medical assessment.

A further advantage of the described method is a simplification of the compensation system for radiologists. The data 13 thus likewise contain billing codes that can be associated with the corresponding regions 5, 7 and 9. This is not possible with whole-body examinations without a definition of regions 5, 7 and 9.

The association of the image datasets with regions 5, 7 and 9 can ensue using the defined regions 5, 7 and 9 both for already-measured image datasets and for image datasets that are yet to be measured. Commercially available magnetic resonance apparatuses can associate corresponding positions of image datasets using an overview image.

Although modifications and changes may be suggested by those skilled in the art, it is the intention of the inventor to embody within the patent warranted hereon all changes and modifications as reasonably and properly come within the scope of her contribution to the art.

I claim:

1. A method for associating data with diagnostic medical image datasets, comprising the steps of:
   from a processor, causing an overview image of an examination subject to be displayed at a display connected to the processor, said overview image representing an entirety of the body of the examination subject;
   via an input unit connected to the processor, designating at least one region, as a designated region, in the displayed overview image, said designated region encompassing only a portion of the entirety of the body of the examination shown in the overview image;
   in said processor, automatically associating text data with the designated region;
   acquiring a diagnostic medical image dataset representing the designated region of the examination subject and, in said processor, automatically associating said diagnostic medical image dataset with the designated region;
   in said processor, automatically associating said text data with said diagnostic medical image dataset using the association of said text data with said designated region and the association of said designated region with the diagnostic medical image dataset; and
   generating a data file comprising said diagnostic medical image dataset associated with said text data and making said data file available at an output of said processor in a form allowing use of the data file to simultaneously display a diagnostic medical image, generated from the diagnostic medical image dataset, and the associated text data.

2. A method as claimed in claim 1 comprising selecting said data from a plurality of predetermined data items.

3. A method as claimed in claim 1 comprising embodying information in said data describing the at least one region associated with the data.

4. A method as claimed in claim 1 comprising embodying instructions in said data for evaluation of said at least one medical image dataset associated with said data.

5. A method as claimed in claim 1 comprising further processing said medical range dataset associated with said data, dependent on said data.

6. A method as claimed in claim 1 comprising, in said processor, dividing said medical image dataset into a plurality of partial image datasets dependent on multiple respective regions of said examination subject on said overview image, and respectively associating data with said plurality of partial image datasets.

7. A method as claimed in claim 1 comprising storing said data in a DICOM header of the medical image dataset associated with the data.

* * * * *